United States Patent
Yoneya

(10) Patent No.: US 11,941,835 B2
(45) Date of Patent: *Mar. 26, 2024

(54) EYE INFORMATION ESTIMATE APPARATUS, EYE INFORMATION ESTIMATE METHOD, AND PROGRAM

(71) Applicant: NIPPON TELEGRAPH AND TELEPHONE CORPORATION, Tokyo (JP)

(72) Inventor: Makoto Yoneya, Tokyo (JP)

(73) Assignee: NIPPON TELEGRAPH AND TELEPHONE CORPORATION, Tokyo (JP)

(*) Notice: Subject to any disclaimer, the term of this patent is extended or adjusted under 35 U.S.C. 154(b) by 487 days.

This patent is subject to a terminal disclaimer.

(21) Appl. No.: 17/271,074

(22) PCT Filed: Aug. 8, 2019

(86) PCT No.: PCT/JP2019/031292
§ 371 (c)(1),
(2) Date: Feb. 24, 2021

(87) PCT Pub. No.: WO2020/045023
PCT Pub. Date: Mar. 5, 2020

(65) Prior Publication Data
US 2021/0319583 A1    Oct. 14, 2021

(30) Foreign Application Priority Data
Aug. 30, 2018    (JP) ................. 2018-161041

(51) Int. Cl.
*G06T 7/70*    (2017.01)
*G06T 7/62*    (2017.01)
*G06V 40/19*   (2022.01)

(52) U.S. Cl.
CPC .............. *G06T 7/70* (2017.01); *G06T 7/62* (2017.01); *G06V 40/19* (2022.01)

(58) Field of Classification Search
CPC ...... G06V 40/19; G06V 40/193; G06V 40/18; G06V 40/197; G06V 10/44; G06V 40/165;
(Continued)

(56) References Cited

U.S. PATENT DOCUMENTS 5,471,542 A * 11/1995 Ragland ................. G06V 40/19
382/128
10,417,495 B1 * 9/2019 Davami ................. G06V 40/19
(Continued)

FOREIGN PATENT DOCUMENTS

| EP | 1842152 B1 * | 1/2011 | ......... G06K 9/00597 |
| JP | 2008264341 A * | 11/2008 | |
| JP | 2011115460 A * | 6/2011 | |

OTHER PUBLICATIONS

Tobii pro, [online], [Retrieved on Jun. 6, 2018], Internet URL:https://www.tobiipro.com/ja/?gclid=EAlaIQobChM19dzRgfq92wIVIYeP-Ch211ge6EAAYAASAAEgLqy_D_BWE.
(Continued)

*Primary Examiner* — Ian L Lemieux
*Assistant Examiner* — Woo C Rhim

(57) ABSTRACT

A technology capable of estimating information on a position and a size of a pupil or an iris using an image obtained by photographing eyes of a subject even when a part of the pupil or the iris is hidden in the image is provided. An eye information estimate apparatus includes a profile determination information acquisition unit configured to acquire, from an image obtained by photographing an eye of a subject, coordinates (x1, y0) and (x2, y0) of two points of a point P1 and a point P2 respectively corresponding to an
(Continued)

outer edge of a pupil or an iris on a predetermined line included in the image and, in a case when a shape of the pupil or the iris is assumed to be an ellipse, slopes θ1 and θ2 of tangent lines of the ellipse at the point P1 and the point P2 respectively from the image, and an eye information calculation unit configured to calculate, R being set a length of a major axis of the ellipse, center coordinates (xc, yc) and an angle of rotation ψ of the ellipse representing a position of the pupil or the iris, and/or a length Rb of a minor axis of the ellipse representing a size of the pupil or the iris using the coordinates (x1, y0) and (x2, y0) of the point P1 and the point P2 respectively, the slopes θ1 and θ2 of the tangent lines of the ellipse at the point P1 and the point P2 respectively, and the length R of the major axis of the ellipse.

5 Claims, 3 Drawing Sheets

(58) Field of Classification Search
CPC ......... A61B 3/113; A61B 3/0025; A61B 3/14; A61B 3/112; A61B 3/11; G06T 2207/30041; G06T 7/13; G06T 7/70; G06T 7/62; G06T 2207/10016; G06T 7/0016
See application file for complete search history.

(56) References Cited

U.S. PATENT DOCUMENTS

| | | | |
|---|---|---|---|
| 2004/0004723 A1* | 1/2004 | Seko | G06F 3/0346 356/498 |
| 2006/0170865 A1* | 8/2006 | Hirohara | A61B 3/0025 351/205 |
| 2007/0133879 A1* | 6/2007 | Fukaya | G06V 10/753 382/190 |
| 2013/0083976 A1* | 4/2013 | Ragland | A61B 3/113 382/117 |
| 2014/0268047 A1* | 9/2014 | Hirsh | A61B 3/112 351/246 |
| 2015/0029322 A1* | 1/2015 | Ragland | G06V 40/19 348/78 |
| 2016/0225153 A1* | 8/2016 | Kim | G06V 40/193 |
| 2017/0286771 A1* | 10/2017 | Ishii | A61B 3/113 |
| 2018/0095295 A1* | 4/2018 | Chene | A61B 3/113 |
| 2018/0350070 A1* | 12/2018 | Ishii | G06T 7/70 |
| 2019/0076012 A1* | 3/2019 | Kobayashi | A61B 3/107 |
| 2021/0223859 A1* | 7/2021 | Sun | G06V 10/764 |
| 2021/0228075 A1* | 7/2021 | Zhang | G06T 7/62 |
| 2021/0393125 A1* | 12/2021 | Yoneya | A61B 3/14 |

OTHER PUBLICATIONS

Nystrom et al. (2013) "Post-saccadic oscillations in eye movement data recorded with pupil-based eye trackers reflect motion of the pupil inside the iris", Vision Research, vol. 92, pp. 59-66.

* cited by examiner

EYE INFORMATION ESTIMATE APPARATUS, EYE INFORMATION ESTIMATE METHOD, AND PROGRAM

CROSS-REFERENCE TO RELATED APPLICATIONS

This application is a U.S. 371 Application of International Patent Application No. PCT/JP2019/031292, filed on 8 Aug. 2019, which application claims priority to and the benefit of JP Application No. 2018-161041, filed on 30 Aug. 2018, the disclosures of which are hereby incorporated herein by reference in their entireties.

TECHNICAL FIELD

The present invention relates to a technology for estimating information on a position and a size of a pupil or an iris.

BACKGROUND ART

It is known that a size of a pupil changes depending on luminance of an area that a person is viewing or a psychological state of the person. It is possible to estimate, for example, a degree of salience of sound by using a change in a size or a position of the pupil (Reference Patent Literature 1).
(Reference Patent Literature 1: JP 2015-132783 A)
A dedicated device called an eye movement measurement device (Non Patent Literature 1) or a method described in Non Patent Literature 2, for example, can be used for estimation of a change in a size or a position of a pupil used in Reference Patent Literature 1.

CITATION LIST

Non Patent Literature

Non Patent Literature 1: tobii pro, [online], [Retrieved on Jun. 6, 2018], Internet URL: www.tobiipro.com
Non Patent Literature 2: Nystrom, M. Hooge, I., Holmqvist, K., "Post-saccadic oscillations in eye movement data recorded with pupil-based eye trackers reflect motion of the pupil inside the iris", Vision Research, Vol. 92, pp. 59-66, 2013.

SUMMARY OF THE INVENTION

Technical Problem

A typical eye movement measurement device as in Non Patent Literature 1 measures a size of a pupil using an image captured by a camera. Specifically, the eye movement measurement device detects an edge (an outer edge) of the pupil from the captured image, and applies circle fitting to a set of points of the detected edge to find a pupil diameter and a center position of the pupil. Thus, it is necessary for the entire pupil to be included in the captured image, and there is a problem in that the pupil diameter is underestimated in a half-blinking state and the center position of the pupil also shifts. Further, because upper and lower sides of an iris are normally covered by eyelids, the iris cannot be detected by a commercially available eye movement measurement device.
In Non Patent Literature 2, because a center position of the iris is found by scanning the eye in a horizontal direction with reference to the center position of the pupil to detect the edge of the iris, the same position is always output in a vertical direction for a center of the pupil and a center of the iris. Thus, in the method of Non Patent Literature 2, position information in the vertical direction is not reliable. Further, for position information in the horizontal direction also, accurate information cannot be obtained in the method of Non Patent Literature 2 when the center position of the iris and the center position of the pupil vertically shift.

Thus, an object of the present invention is to provide a technology capable of estimating information on a position and a size of a pupil or an iris using an image obtained by photographing eyes of a subject even when a part of the pupil or the iris is hidden in the image.

Means for Solving the Problem

An aspect of the present invention is an eye information estimate apparatus including a profile determination information acquisition unit configured to acquire, from an image obtained by photographing an eye of a subject, coordinates $(x_1, y_0)$ and $(x_2, y_0)$ of two points of a point P1 and a point P2 respectively corresponding to an outer edge of a pupil or an iris on a predetermined line included in the image and, in a case when a shape of the pupil or the iris is assumed to be an ellipse, slopes $\theta_1$ and $\theta_2$ of tangent lines of the ellipse at the point P1 and the point P2 respectively from the image, and an eye information calculation unit configured to calculate, R being set a length of a major axis of the ellipse, center coordinates $(x_c, y_c)$ and an angle of rotation $\psi$ of the ellipse representing a position of the pupil or the iris, and/or a length $R_b$ of a minor axis of the ellipse representing a size of the pupil or the iris using the coordinates $(x_1, y_0)$ and $(x_2, y_0)$ of the point P1 and the point P2 respectively, the slopes $\theta_1$ and $\theta_2$ of the tangent lines of the ellipse at the point P1 and the point P2 respectively, and the length R of the major axis of the ellipse.

Effects of the Invention

According to the present invention, it is possible to estimate information on a position and a size of a pupil or an iris using an image obtained by photographing eyes of a subject even when a part of the pupil or the iris is hidden in the image.

DESCRIPTION OF EMBODIMENTS

Figure 1:
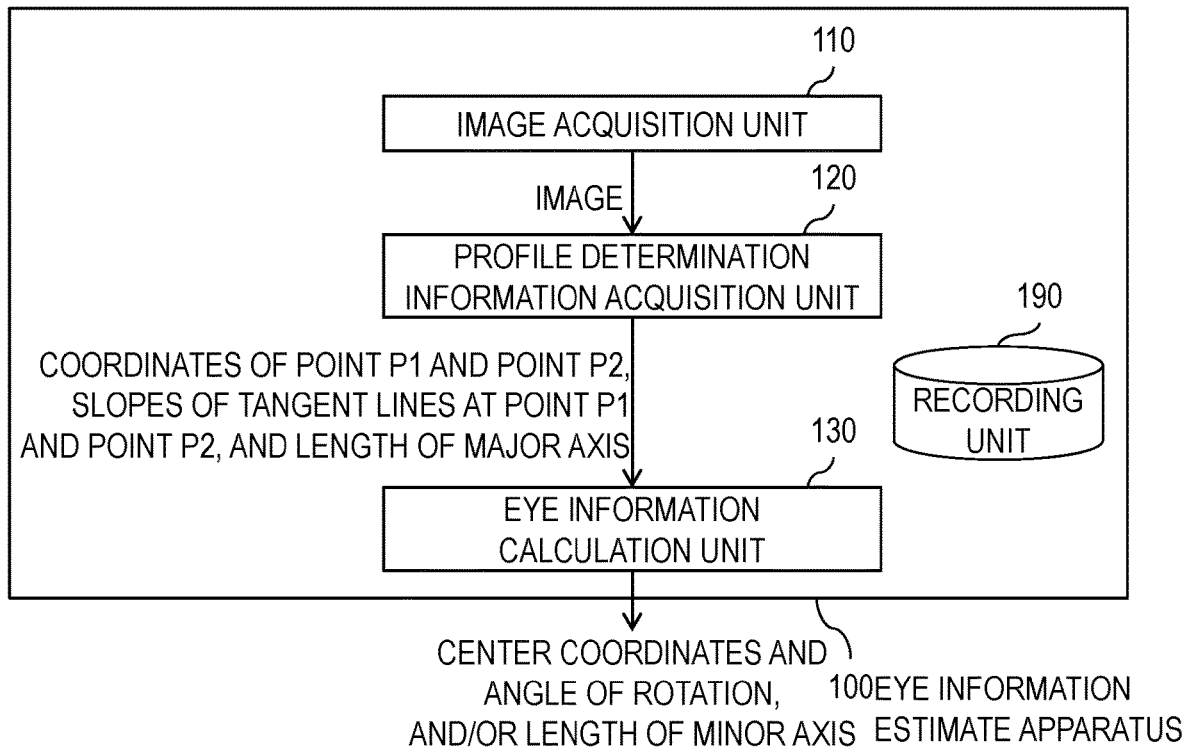
FIG. 1 is a block diagram illustrating an example of a configuration of an eye information estimate apparatus 100.

Hereinafter, embodiments of the present invention will be described in detail. Components having the same function are denoted by the same reference signs, and redundant description thereof will be omitted.

<Technical Background>

A subject of which position and size information is estimated is a pupil or an iris. Further, an image obtained by photographing an eye of the subject is used for estimation of a position and a size of the pupil or the iris. In the estimation, it is assumed that a shape of the pupil or the iris in the captured image is an ellipse. Thus, the position and the size of the pupil or the iris is estimated as center coordinates, an angle of rotation, a length of a major axis, and a length of a minor axis of the ellipse. Specifically, the center coordinates, the angle of rotation, the length of the major axis, and the length of the minor axis that serve as a profile of the ellipse are estimated from coordinates of two points P1 and P2 corresponding to an outer edge of the pupil or the iris on a predetermined line included in the image obtained by photographing the eye of the subject, and slopes of tangent lines of an ellipse (that is, an ellipse representing the pupil or the iris that is an estimation target) at these points. In this case, it is assumed that the length of the major axis does not change while the image is captured at a predetermined sampling frequency. That is, the length of the major axis can be acquired from the image. Hereinafter, this length will be referred to as R.

Based on this, a problem of estimating the position and the size of the pupil or the iris results in a problem of finding a center coordinates $(x_c, y_c)$, an angle of rotation $\psi$, a length $R_a$ of the major axis, and a length $R_b$ of the minor axis of the ellipse (here, $R_a = R$) from coordinates $(x_1, y_0)$ and $(x_2, y_0)$ of the two points P1 and P2 on the ellipse, slopes $\theta_1$ and $\theta_2$ of tangent lines of the ellipse at the points, and the length R of the major axis of the ellipse.

A method for finding the coordinates $(x_1, y_0)$ and $(x_2, y_0)$ of the points P1 and P2, the slopes $\theta_1$ and $\theta_2$ of the tangent line of the ellipse at the two points, and the length R of the major axis of the ellipse from the image obtained by photographing the eye of the subject will be described below.

Hereinafter, a procedure for solving the above problem will be described. In general, an ellipse at any position on a two-dimensional plane is represented by the following equation.

[Math. 1]

$$\left(\frac{(x-x_c)\cos\psi + (y-y_c)\sin\psi}{R_a}\right)^2 + \left(\frac{-(x-x_c)\sin\psi + (y-y_c)\cos\psi}{R_b}\right)^2 = 1$$

Here, in order to solve the above problem, a coordinate conversion is performed so that an ellipse at an any position corresponds to an ellipse that passes through a point (1, 0) on an x-axis and a point (0, 1) on a y-axis, and comes into contact with the x-axis at the point (1, 0) and the y-axis at the point (0, 1), and calculation is performed using the fact that the ellipse after the conversion is expressed by the following equation.

$$(x-1)^2 + (y-1)^2 + 2\alpha xy = 1 \ (|\alpha| \le 1) \quad [\text{Math. 2}]$$

Here, $\alpha$ denotes a hyperparameter.

Hereinafter, details will be described. Coordinates $(x_s, y_s)$ of the intersection C of the tangent line of the ellipse at the point P1 and the tangent line of the ellipse at the point P2 can be expressed by the following equation using the coordinates $(x_1, y_0)$ and $(x_2, y_0)$ of the points P1 and P2 and the slopes $\theta_1$ and $\theta_2$ of the tangent lines of the ellipse at the two points.

[Math. 3]

$$\begin{pmatrix} x_s \\ y_s \end{pmatrix} = \begin{pmatrix} \frac{x_1 \tan\theta_1 - x_2 \tan\theta_2}{\tan\theta_1 - \tan\theta_2} \\ \frac{(x_1 - x_2)\tan\theta_1 - \tan\theta_2}{\tan\theta_1 - \tan\theta_2} \end{pmatrix} \quad (1)$$

Here, an equation of the ellipse obtained by converting a coordinate system so that the intersection C corresponds to a point (0, 0), the point P1 corresponds to a point (1, 0), and the point P2 corresponds to a point (0, 1) is as follows.

[Math. 4]

$$\vec{q}_1 = \begin{pmatrix} \frac{1}{x_1 - x_2} \\ \frac{1}{(x_1 - x_2)\tan\theta_2} \end{pmatrix}$$

$$\vec{q}_2 = \begin{pmatrix} \frac{-1}{x_1 - x_2} \\ \frac{1}{(x_1 - x_2)\tan\theta_1} \end{pmatrix}$$

$$\vec{x} = \begin{pmatrix} x \\ y \end{pmatrix}$$

This can be expressed as the following equation.

$$(\vec{q}_1 \cdot \vec{x} - 1)^2 + (\vec{q}_2 \cdot \vec{x} - 1)^2 + 2\alpha(\vec{q}_1 \cdot \vec{x})(\vec{q}_2 \cdot \vec{x}) = 1 \quad [\text{Math. 5}]$$

Then, the profile of the ellipse, that is, the center coordinates $(x_c, y_c)$, the angle of rotation $\psi$, the length $R_a$ of the major axis, and the length $R_b$ of the minor axis can be expressed as follows using the hyperparameter $\alpha$.

[Math. 6]

$$x_c = \frac{(x_s - x_s) + (x_2 - x_s)}{\alpha + 1} + x_s \quad (2a)$$

$$y_c = \frac{2(y_0 - y_s)}{\alpha + 1} + y_s \quad (2b)$$

$$\psi = -\frac{1}{2}\arctan\left(\frac{\lambda_1 + \lambda_2}{1 - \lambda_1\lambda_2\frac{(\lambda_1 + \lambda_2)^2}{2(\alpha - 1)}}\right) \quad (3)$$

$$R_{a,b}^2 = \left(\frac{y_0 - y_s}{\alpha + 1}\right)^2 \left\{\frac{f_1 + f_2}{2} - \alpha f_0 \pm \left\{(f_1\alpha - f_0)(f_2\alpha - f_0) + \left(\frac{f_1 - f_2}{2}\right)^2\right\}\right\} \quad (4)$$

Here,

[Math. 7]

$$x_s = \frac{x_1 \tan\theta_1 - x_2 \tan\theta_2}{\tan\theta_1 - \tan\theta_2} \quad (5a)$$

$$y_s = y_0 + \frac{(x_1 - x_2)\tan\theta_1 \tan\theta_2}{\tan\theta_1 - \tan\theta_2} \quad (5b)$$

$$\lambda_1 = \frac{x_2 - x_s}{y_0 - y_s}\left(=\frac{1}{\tan\theta_1}\right) \quad (6a)$$

$$\lambda_2 = \frac{x_2 - x_s}{y_0 - y_s}\left(=\frac{1}{\tan\theta_2}\right) \quad (6b)$$

$$f_0 = 1 + \lambda_1\lambda_2 \quad (7a)$$

$$f_1 = 1 + \lambda_1^2 \quad (7b)$$

$$f_2 = 1 + \lambda_2^2 \quad (7c)$$

Here, $R_{a,b}^2$ in Equation (4) means $R_a^2$ or $R_b^2$, and among the values on the right side of Equation (4) (that is, the two values represented by using ±), the smaller one is $R_b^2$ and the greater one is $R_a^2$. Further, square roots on the right side of Equation (4) become $R_a$ and $R_b$.

A ratio $r$ (=$R_b/R_a$) of the length of the minor axis to the length of the major axis can also be expressed as follows using the hyperparameter $\alpha$.

[Math. 8]

$$r^2 = \frac{1-a^2}{(1+a)^4} \cdot \frac{(y_0 - y_s)^2(x_1 - x_2)^2}{R_a^4} \quad (8)$$

Hereinafter, Equations (2a) and (2b) are expressions of the center coordinates $(x_c, y_c)$ using the hyperparameter $\alpha$. Similarly, Equation (3) is an expression of the angle of rotation $\psi$ using the hyperparameter $\alpha$, Equation (4) is an expression of the length $R_a$ of the major axis using the hyperparameter $\alpha$ and an expression of the length $R_b$ of the minor axis using the hyperparameter $\alpha$, and Equation (8) is an expression of the ratio $r$ of the length of the minor axis to the length of the major axis using the hyperparameter $\alpha$. Further, the hyperparameter $\alpha$ is also referred to as a hyperparameter that is used for an expression of the elliptic profile.

Thus, when the above expression is used, it is possible to find the center coordinates $(x_c, y_c)$, the angle of rotation $\psi$, and the length $R_b$ of the minor axis by finding the hyperparameter $\alpha$ (where $|\alpha| \leq 1$) at which $R_a = R$ using Equation (4).

First Embodiment

Figure 2:
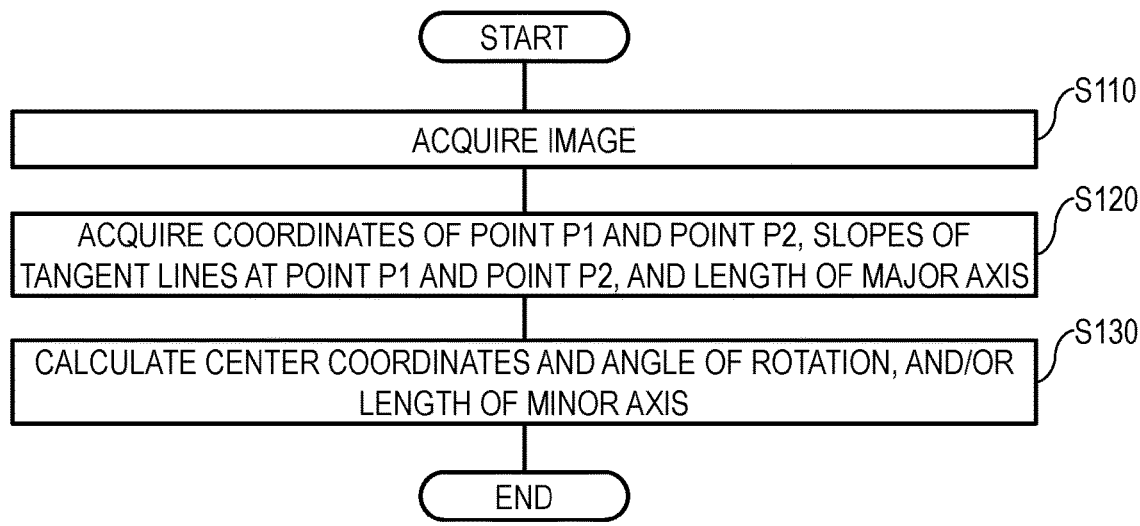
FIG. 2 is a flowchart illustrating an example of an operation of the eye information estimate apparatus 100.

Hereinafter, the eye information estimate apparatus 100 will be described with reference to FIGS. 1 and 2. FIG. 1 is a block diagram illustrating a configuration of the eye information estimate apparatus 100. FIG. 2 is a flowchart illustrating an operation of the eye information estimate apparatus 100. The eye information estimate apparatus 100 includes an image acquisition unit 110, a profile determination information acquisition unit 120, an eye information calculation unit 130, and a recording unit 190, as illustrated in FIG. 1. The recording unit 190 is a component that appropriately records information necessary for processing of the eye information estimate apparatus 100.

An operation of the eye information estimate apparatus 100 will be described with reference to FIG. 2.

[Image Acquisition Unit 110]

In S110, the image acquisition unit 110 acquires and outputs the image obtained by photographing the eye of the subject. Here, although a camera that is used for image capturing is assumed to be a camera having a relatively low sampling frequency such as a camera of a smartphone, a camera having a high sampling frequency may be used. The camera may be set to photograph both of left and right eyes or may be set to photograph only one of the eyes. Hereinafter, it is assumed that the camera is set to photograph only one of the eyes.

[Profile Determination Information Acquisition Unit 120]

In S120, the profile determination information acquisition unit 120 receives the image acquired in S110 as an input, acquires coordinates $(x_1, y_0)$ and $(x_2, y_0)$ of two points P1 and P2 corresponding to an outer edge of the pupil or the iris on a predetermined line included in the image, slopes $\theta_1$ and $\theta_2$ of tangent lines of the ellipse at the points P1 and P2 in a case when a shape of the pupil or the iris is assumed to be an ellipse, and the length R of the major axis of the ellipse, as the profile determination information, and outputs these. Hereafter, a method for acquiring the coordinates $(x_1, y_0)$ and $(x_2, y_0)$ of the points P1 and P2, the slopes $\theta_1$ and $\theta_2$ of the tangent lines of the ellipse at the points P1 and P2, and the length R of the major axis of the ellipse will be described.

The coordinates $(x_1, y_0)$ and $(x_2, y_0)$ of the points P1 and P2 can be acquired, for example, by detecting an area or a boundary of the pupil or the iris using a method described in Reference Non Patent Literature 1.

(Reference Non Patent Literature 1: Daugman, J, "Probing the uniqueness and randomness of Iris Codes: Results from 200 billion iris pair comparisons", Proceedings of the IEEE, Vol. 94, No. 11, pp. 1927-1935, 2006.)

Figure 3:
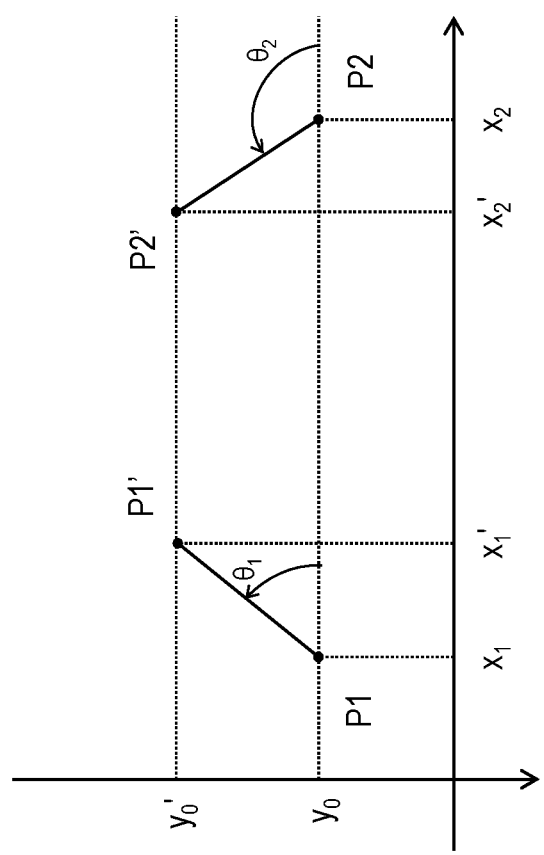
FIG. 3 is a diagram illustrating an example of four points corresponding to an outer edge of a pupil (iris) on two adjacent lines.

The slopes $\theta_1$ and $\theta_2$ of the tangent lines of the ellipse at the points P1 and P2 can be acquired using coordinates of points corresponding to the outer edge of the pupil or the iris on a line adjacent to the predetermined line and the coordinates $(x_1, y_0)$ and $(x_2, y_0)$ of the points P1 and P2. Specifically, the slopes $\theta_1$ and $\theta_2$ are found as follows. First, coordinates of two points P1' and P2' corresponding to the outer edge of the pupil or the iris on the line located on the upper side in the image among the lines adjacent to the predetermined line are set to $(x_1', y_0')$ and $(x_2', y_0')$, and slopes $\theta_1'$ and $\theta_2'$ are found using the following equations (see FIG. 3).

[Math. 9]

$$\theta_1' = \arctan\frac{y_0' - y_0}{x_1' - x_1}$$

$$\theta_2' = \arctan\frac{y_0' - y_0}{x_2' - x_2}$$

Similarly, coordinates of two points P1" and P2" corresponding to the outer edge of the pupil or the iris on the line located on the lower side in the image among the lines adjacent to the predetermined line are set to $(x_1", y_0")$ and $(x_2", y_0")$, and slopes $\theta_1"$ and $\theta_2"$ are found using the following equations.

[Math. 10]

$$\theta_1'' = \arctan\frac{y_0'' - y_0}{x_1'' - x_1}$$

$$\theta_2'' = \arctan\frac{y_0'' - y_0}{x_2'' - x_2}$$

Then, the slopes $\theta_1$ and $\theta_2$ are found by the following equations using the slopes $\theta_1'$, $\theta_2'$, $\theta_1"$, and $\theta_2"$.

[Math. 11]

$$\theta_1 = \frac{\theta_1' + \theta_1''}{2}$$

$$\theta_2 = \frac{\theta_2' + \theta_2''}{2}$$

That is, the slopes $\theta_1$ and $\theta_2$ are found as an average value of a slope calculated using coordinates of two points corresponding to the outer edge of the pupil or the iris on the line located on the upper side in the image among the lines adjacent to the predetermined line and the coordinates $(x_1, y_0)$ and $(x_2, y_0)$ of the points P1 and P2, and a slope calculated using coordinates of two points corresponding to the outer edge of the pupil or the iris on the line located on the lower side in the image among the lines adjacent to the predetermined line and the coordinates $(x_1, y_0)$ and $(x_2, y_0)$ of the points P1 and P2.

The length R of the major axis of the ellipse is acquired as the length of the major axis resulting from ellipse fitting on the outer edge of the pupil or the iris included in the image.

[Eye Information Calculation Unit 130]

In S130, the eye information calculation unit 130 receives the coordinates $(x_1, y_0)$ and $(x_2, y_0)$ of the points P1 and P2, the slopes $\theta_1$ and $\theta_2$ of the tangent lines of the ellipse at the points P1 and P2, and the length R of the major axis of the ellipse acquired in S120 as inputs, calculates the center coordinates $(x_c, y_c)$ and the angle of rotation $\psi$ of the ellipse representing the position of the pupil or the iris, and/or the length $R_b$ of the minor axis of the ellipse representing the size of the pupil or the iris using the coordinates $(x_1, y_0)$ and $(x_2, y_0)$ of the points P1 and P2, the slopes $\theta_1$ and $\theta_2$ of the tangent lines of the ellipse at the points P1 and P2, and the length R of the major axis of the ellipse, and outputs the center coordinates $(x_c, y_c)$ and the angle of rotation $\psi$ of the ellipse and/or the length $R_a$ of the major axis and the length $R_b$ of the minor axis of the ellipse. For the length $R_a$ of the major axis, the input value R may be output.

Figure 4:
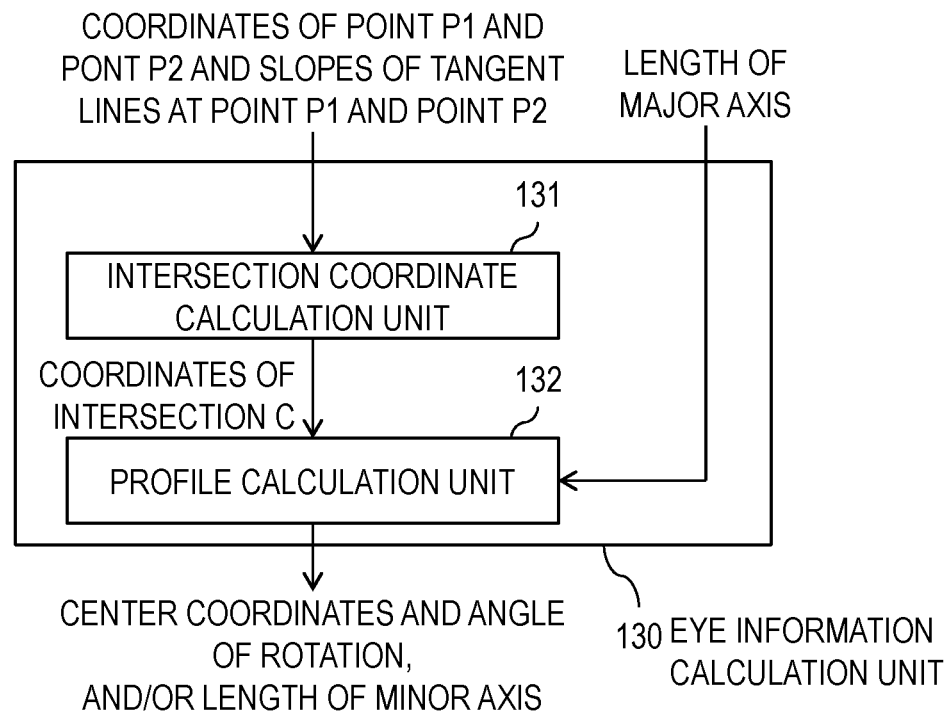
FIG. 4 is a block diagram illustrating an example of a configuration of an eye information calculation unit 130.
Figure 5:
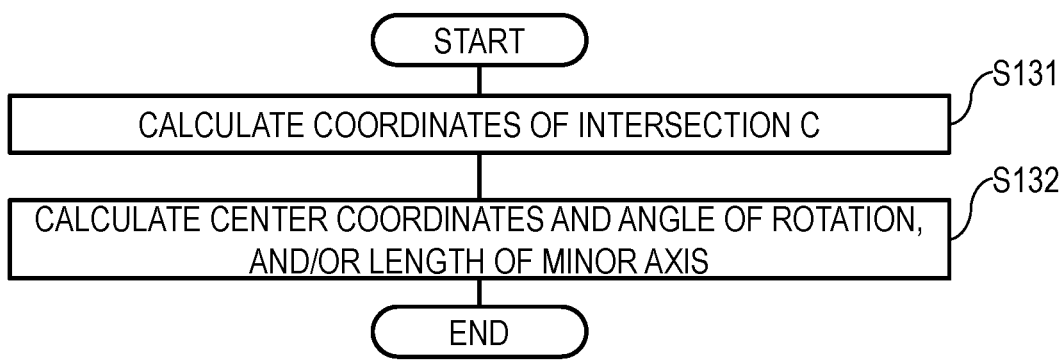
FIG. 5 is a flowchart illustrating an example of an operation of the eye information calculation unit 130.

Hereinafter, the eye information calculation unit 130 will be described with reference to FIGS. 4 to 5. FIG. 4 is a block diagram illustrating a configuration of the eye information calculation unit 130. FIG. 5 is a flowchart illustrating an operation of the eye information calculation unit 130. The eye information calculation unit 130 includes an intersection coordinate calculation unit 131 and a profile calculation unit 132, as illustrated in FIG. 4.

An operation of the eye information calculation unit 130 will be described with reference to FIG. 5.

[Intersection Coordinate Calculation Unit 131]

In S131, the intersection coordinate calculation unit 131 calculates the coordinates $(x_s, y_s)$ of the intersection C of the tangent lines using the coordinates $(x_1, y_0)$ and $(x_2, y_0)$ of the points P1 and P2 and the slopes $\theta_1$ and $\theta_2$ of the tangent lines of the ellipse at the points P1 and P2. Specifically, the coordinates $(x_s, y_s)$ of the intersection C are calculated using Equation (1).

[Profile Calculation Unit 132]

In S132, the profile calculation unit 132 finds the hyperparameter $\alpha$ (where $|\alpha| \leq 1$) using the coordinates $(x_1, y_0)$ and $(x_2, y_0)$ of the points P1 and P2 and the coordinates $(x_s, y_s)$ of the intersection C calculated in S131 to calculate the center coordinates $(x_c, y_c)$ and the angle of rotation $\psi$ of the ellipse, and/or the length $R_b$ of the minor axis of the ellipse. Hereinafter, details will be described.

First, the profile calculation unit 132 finds an expression (that is, Equation (4)) of the length $R_a$ of the major axis using the hyperparameter $\alpha$ using the coordinates $(x_1, y_0)$ and $(x_2, y_0)$ of the points P1 and P2 and the coordinates $(x_s, y_s)$ of the intersection C.

The profile calculation unit 132 then determines the hyperparameter $\alpha$ using the expression of the length $R_a$ of the major axis of Equation (4) and the length R of the major axis. Specifically, $\alpha$ ($|\alpha| \leq 1$) at which a value of Equation (4) becomes R is found. In a case when $\alpha$ at which a value of Equation (4) becomes R does not satisfy $|\alpha| \leq 1$, a determination is made that the position and size of the pupil or the iris cannot be estimated from the image (estimation is impossible), and profile calculation to be described below is not performed.

The profile calculation unit 132 calculates the center coordinates $(x_c, y_c)$ and the angle of rotation $\psi$ of the ellipse from Equations (2a), (2b), and (3) using the determined $\alpha$. Further, the profile calculation unit 132 calculates the length $R_b$ of the minor axis of the ellipse from Equation (4) using the determined $\alpha$. The eye information calculation unit 130 may calculate only the center coordinates $(x_c, y_c)$ and the angle of rotation $\psi$ of the ellipse when the eye information calculation unit 130 outputs a profile representing the position of the pupil or the iris as the eye information, and may calculate only the length $R_b$ of the minor axis of the ellipse when the eye information calculation unit 130 outputs a profile representing the size of the pupil or the iris as the eye information.

When an image obtained by photographing both the left and right eyes is used, the processes from S120 to S130 may be executed for each of the eyes.

According to the embodiment of the present invention, even when a part of the pupil or the iris is hidden in the image obtained by photographing the eyes of the subject, it is possible to estimate information on the position and the size of the pupil or the iris using the image.

<First Modification>

A case in which the length R of the major axis is acquired from the image has been described above. However, the present invention is not limited to this method, and the length R of the major axis may be found by another method and used. For example, because a size of an iris of an adult does not greatly change with time, an estimated value of the length R of the major axis may be calculated on the basis of a distance between a camera and an eye and used when the size of the iris was already found in the past and held as data. In this case, for example, the length R of the major axis may be recorded in the recording unit 190 in advance.

<Second Modification>

Although a case in which the profile (the profile representing the position and the size of the pupil or the iris) is calculated from the profile determination information regarding a predetermined line in the image has been described above, a profile calculation method is not limited to this method. For example, a plurality of profiles may be acquired by repeatedly executing the processes of S120 to S130 for a plurality of lines (including (a part of) an ellipse) in the same image, and a representative value (for example, an average value) found from the plurality of acquired profiles may be output as a profile.

APPENDIX

The device of the present invention includes, for example, as single hardware entities, an input unit to which a keyboard or the like can be connected, an output unit to which a liquid crystal display or the like can be connected, a communication unit to which a communication device (for example, a communication cable) capable of communication with the outside of the hardware entity can be connected, a Central Processing Unit (CPU, which may include a cache memory, a register, and the like), a RAM or a ROM that is a memory, an external storage device that is a hard disk, and a bus connected for data exchange with the input unit, the output unit, the communication unit, the CPU, the RAM, the ROM, and the external storage devices. Further, a device (drive) capable of reading and writing from and to a recording medium such as a CD-ROM may be provided in the hardware entity as necessary. An example of a physical entity including such hardware resources is a general-purpose computer.

A program necessary to implement the above-described functions, data necessary for processing of this program, and the like are stored in the external storage device of the hardware entity (the present invention is not limited to the external storage device; for example, the program may be read out and stored in a ROM that is a dedicated storage device). Further, for example, data obtained by the processing of the program is appropriately stored in a RAM, the external storage device, or the like.

In the hardware entity, each program and data necessary for the processing of each program stored in the external storage device (or a ROM, for example) are read into a memory as necessary and appropriately interpreted, executed, or processed by a CPU. As a result, the CPU implements a predetermined function (each of components represented by xxx unit, xxx means, or the like).

The present invention is not limited to the above-described embodiment, and appropriate changes can be made without departing from the spirit of the present invention. Further, the processing described in the embodiments are not only executed in time series in the described order, but also may be executed in parallel or individually according to a processing capability of a device that executes the processing or as necessary.

As described above, when a processing function in the hardware entity (the device of the present invention) described in the embodiment is implemented by a computer, processing content of a function that the hardware entity should have is described by a program. By executing this program using the computer, the processing function in the hardware entity is implemented on the computer.

A program describing this processing content can be recorded on a computer-readable recording medium. An example of the computer-readable recording medium may include any recording medium such as a magnetic recording device, an optical disc, a magneto-optical recording medium, and a semiconductor memory. Specifically, for example, a hard disk device, a flexible disk, a magnetic tape, or the like can be used as a magnetic recording device/medium, a Digital Versatile Disc (DVD), a DVD-Random Access Memory (RAM), a Compact Disc Read Only Memory (CD-ROM), CD-R (Recordable)/RW (ReWritable), or the like can be used as an optical disc, a Magneto-Optical disc (MO) or the like can be used as a magneto-optical recording medium, and an Electrically Erasable and Programmable-Read Only Memory (EEP-ROM) or the like can be used as a semiconductor memory.

Further, this program is distributed by, for example, selling, transferring, or lending a portable recording medium such as a DVD or a CD-ROM on which the program has been recorded. Further, the program may be stored in a storage device of a server computer and distributed by being transferred from the server computer to another computer via a network.

The computer that executes such a program first temporarily stores, for example, the program recorded on the portable recording medium or the program transferred from the server computer in a storage unit of the computer. When the computer executes the processing, the computer reads the program stored in the storage unit of the computer and executes a process according to the read program. Further, as another embodiment of executing the program, the computer may directly read the program from the portable recording medium and execute processing according to the program, and further, processing according to a received program may be sequentially executed each time the program is transferred from the server computer to the computer. Further, a configuration in which the above-described process is executed by a so-called Application Service Provider (ASP) type service for implementing a processing function according to only an execution instruction and result acquisition without transferring the program from the server computer to the computer may be adopted. It is assumed that the program in the present embodiment includes information provided for processing by an electronic calculator and being equivalent to the program (such as data that is not a direct command to the computer, but has properties defining processing of the computer).

Further, although the hardware entity is configured by a predetermined program being executed on the computer in the present embodiment, at least a part of the processing content of the hardware entity may be implemented in hardware.

The invention claimed is:

1. An eye information estimate apparatus for estimating eye information from an image of an eye with a partial showing of a pupil or an iris, the apparatus comprising a processor configured to execute operations comprising:
   acquiring, from the image of the eye with the partial showing of the pupil or the iris obtained by photographing the eye of a subject by a camera, coordinates $(x_1, y_0)$ and $(x_2, y_0)$ of two points of a point P1 and a point P2 respectively corresponding to an outer edge of a pupil or an iris on a predetermined line included in the image and, based on recognizing a shape of the pupil or the iris as an ellipse, slopes $\theta_1$ and $\theta_2$ of tangent lines of the ellipse at the point P1 and the point P2 respectively from the image;
   calculating, R being set a length of a major axis of the ellipse, center coordinates $(x_c, y_c)$ and an angle of rotation $\psi$ of the ellipse representing a position of the pupil or the iris, and/or a length $R_b$ of a minor axis of the ellipse representing a size of the pupil or the iris using the coordinates $(x_1, y_0)$ and $(x_2, y_0)$ of the point P1 and the point P2 respectively, the slopes $\theta_1$ and $\theta_2$ of the tangent lines of the ellipse at the point P1 and the point P2 respectively, and the length R of the major axis of the ellipse; and
   generating, based on the partial showing of the pupil or the iris of the eye in the image, a profile of the eye of the subject, wherein the profile includes:
      the center coordinates $(x_c, y_c)$ and the angle of rotation $\psi$ of the ellipse to represent the position of the pupil or the iris as a whole, and
      the length $R_b$ of the minor axis of the ellipse to represent the size of the pupil or the iris as a whole.

2. The eye information estimate apparatus according to claim 1,
   wherein the calculating the center coordinates $(x_c, y_c)$ and the angle of rotation $\psi$ and/or the length $R_b$ further comprises:
      calculating, using the coordinates $(x_1, y_0)$ and $(x_2, y_0)$ of the point P1 and the point P2 respectively and the slopes $\theta_1$ and $\theta_2$ of the tangent lines of the ellipse at the point P1 and the point P2 respectively, coordinates $(x_s, y_s)$ of an intersection C of the tangent lines; and
      finding a hyperparameter $\alpha$ (where $|\alpha| \leq 1$) using the coordinates $(x_1, y_0)$ and $(x_2, y_0)$ of the point P1 and the point P2 respectively and the coordinates $(x_s, y_s)$ of the intersection C to calculate the center coordinates $(x_c, y_c)$ and the angle of rotation $\psi$ of the ellipse, and/or the length $R_b$ of the minor axis of the ellipse.

3. The eye information estimate apparatus according to claim 1,
wherein the acquiring the coordinates $(x_1, y_0)$ and $(x_2, y_0)$ and the slopes $\theta_1$ and $\theta_2$ further comprises acquiring the slopes $\theta_1$ and $\theta_2$ of the tangent lines of the ellipse at the point P1 and the point P2 respectively using coordinates of points corresponding to the outer edge of the pupil or the iris on a line adjacent to the predetermined line and the coordinates $(x_1, y_0)$ and $(x_2, y_0)$ of the point P1 and the point P2 respectively.

4. An eye information estimate method for estimating eye information from an image of an eye with a partial showing of a pupil or an iris, the method comprising:
a profile determination information acquisition step in which an eye information estimate apparatus acquires, from the image of the eye with the partial showing of the pupil or the iris obtained by photographing the eye of a subject by a camera, coordinates $(x_1, y_0)$ and $(x_2, y_0)$ of two points of a point P1 and a point P2 respectively corresponding to an outer edge of a pupil or an iris on a predetermined line included in the image and, based on recognizing a shape of the pupil or the iris as an ellipse, slopes $\theta_1$ and $\theta_2$ of tangent lines of the ellipse at the point P1 and the point P2 respectively from the image; and
an eye information calculation step in which the eye information estimate apparatus calculates, R being set a length of a major axis of the ellipse, center coordinates $(x_c, y_c)$ and an angle of rotation $\psi$ of the ellipse representing a position of the pupil or the iris, and/or a length $R_b$ of a minor axis of the ellipse representing a size of the pupil or the iris using the coordinates $(x_1, y_0)$ and $(x_2, y_0)$ of the point P1 and the point P2 respectively, the slopes $\theta_1$ and $\theta_2$ of the tangent lines of the ellipse at the point P1 and the point P2 respectively, and the length R of the major axis of the ellipse; and
generate, based on the partial showing of the pupil or the iris of the eye in the image, a profile of the eye of the subject, wherein the profile includes:
the center coordinates $(x_c, y_c)$ and the angle of rotation $\psi$ of the ellipse to represent the position of the pupil or the iris as a whole, and
the length $R_b$ of the minor axis of the ellipse to represent the size of the pupil or the iris as a whole.

5. A non-transitory computer-readable storage medium which stores a program for causing a computer to function as the eye information estimate apparatus according to claim 1.

* * * * *